United States Patent
Ruano et al.

(10) Patent No.: US 9,558,320 B2
(45) Date of Patent: Jan. 31, 2017

(54) PHYSIOGENOMIC METHOD FOR PREDICTING DRUG METABOLISM RESERVE FOR ANTIDEPRESSANTS AND STIMULANTS

(75) Inventors: Gualberto Ruano, Milford, CT (US); David Victor Villagra, West Hartford, CT (US); Mohan Ranjit Kumar Kocherla, Hartford, CT (US); Andreas Windemuth, South Glastonbury, CT (US); John W. Goethe, Avon, CT (US)

(73) Assignee: GENOMAS, INC., Hartford, CT (US)

( * ) Notice: Subject to any disclaimer, the term of this patent is extended or adjusted under 35 U.S.C. 154(b) by 230 days.

(21) Appl. No.: 12/910,165

(22) Filed: Oct. 22, 2010

(65) Prior Publication Data

US 2011/0098186 A1  Apr. 28, 2011

Related U.S. Application Data

(60) Provisional application No. 61/254,767, filed on Oct. 26, 2009.

(51) Int. Cl.
| | |
|---|---|
| *C07H 21/04* | (2006.01) |
| *G06F 19/18* | (2011.01) |
| *C12Q 1/68* | (2006.01) |
| *G06F 19/00* | (2011.01) |

(52) U.S. Cl.
CPC .......... *G06F 19/18* (2013.01); *G06F 19/3431* (2013.01)

(58) Field of Classification Search
CPC ...... G06F 19/18; G06F 19/3431; G06F 19/24; G06F 19/3437; C12Q 1/6883; C12Q 2600/106; C12Q 2600/156; C12Q 2600/16
See application file for complete search history.

(56) References Cited

U.S. PATENT DOCUMENTS

| 7,747,392 | B2 | 6/2010 | Ruano et al. |
|---|---|---|---|
| 2006/0278241 | A1 | 12/2006 | Ruano |
| 2007/0003931 | A1 | 1/2007 | Mrazek et al. |
| 2007/0202518 | A1 | 8/2007 | Ruano et al. |
| 2008/0070253 | A1* | 3/2008 | Buela et al. ............... 435/6 |
| 2008/0311563 | A1 | 12/2008 | Mrazek et al. |
| 2009/0075254 | A1 | 3/2009 | Ruano et al. |

OTHER PUBLICATIONS

Black, J.L. et al., Expert Opinion Drug Metab. Toxicol., vol. 3, pp. 21-31 (2007).*
Porcelli, S. et al., Expert Opinion Drug Metab. Toxicol., vol. 7, pp. 1101-1115 (2011).*
Nakamoto, K. et al., Pharmacogenet. Genomics, vol. 17, pp. 103-114 (2007).*
FDA 510(k) Premarket Notification for AmpliChip CYP450 Test, pp. 1-19 plus 2 cover pages (Dec. 2004).*
Raimundo, S. et al., Clin. Pharmacol. Ther., vol. 76, pp. 128-138 (2004).*
CYP2D6 gene allele nomenclature (downloaded from www.cypalleles.ki.se/cyp2d6.htm Feb. 14, 2014).*
Thakur, M. et al., Genetics in Medicine, vol. 9, pp. 826-835 (2007).*
Premera Blue Cross Medical Policy: Genetic Testing for Mental Health Conditions, revised Dec. 17, 2014 (downloaded from www.premera.com/medicalpolicies/CMI_155669.htm).*
Pickering, J.W. et al., Am. J. Pharmacogenomics, vol. 4, pp. 199-207 (2004).*
Sistonen, J. et al., Clin. Chem., vol. 51 pp. 1291-1295 (2005).*
Melis, R. et al., Expert Rev. Mol. Diagn., vol. 6, pp. 811-820 (2006).*
Ingelman-Sundberg, M. et al., Pharmacology & Therapeutics, vol. 116, pp. 496-526 (2007).*
Ruano, et al.; "Increased Carrier Prevalence of Deficient CYP2C9, CYP2C19 and CYP2D6 Alleles in Depressed Patients Referred to a Tertiary Psychiatric Hospital"; Personalized Medicine in Action; 5; pp. 579-587; (2008).
Ruano, et al.; "Somatic Complications of Psychotropic Medications in a Patient with Multiple CYP2 Drug Metabolism Deficiencies"; Connecticut Medicine; 71; pp. 197-200; (2007).
Landino et al.; "Case Study: Guidance of Pharmacotherapy in a Complex Psychiatric Case by CYP450 DNA typing"; Journal of the American Academy of Nurse Practitioners; 23; pp. 459-463; (2011).
Future Science Group Press Release; "Companion Studies Offer Promise for Personalized Management of Psychotropic Therapy"; www.futuremedicine.com; printed Jul. 2011; 2 pages.
Ruano et al.; "Physiogenomic Analysis of CYP450 Drug Metabolism Correlates Dyslipidemia with Pharmacogenetic Functional Status in Psychiatric Patients"; Biomarkers Med.; 5(4); p. 439-449; (2011).
Villagra et al.; "Novel Drug Metabolism Indices for Pharmacogenetic Functional Status Based on Combinatory Genotyping of CYP2C9, CYP2C19 and CYP2D6 Genes"; Biomarkers Med. 5(4); pp. 427-438; (2011).
"Custom TaqMan SNP Genotyping Assays Simplify Your Genomic Projects"; Product Bulletin TaqMan Genotyping Assays; from Applied Biosystems; Publication 135PB01-02, 2007,2010; www.appliedbiosystems.com.

* cited by examiner

*Primary Examiner* — Teresa Strzelecka
(74) *Attorney, Agent, or Firm* — Cantor Colburn LLP

(57) ABSTRACT

Disclosed herein are compositions and methods relevant to a novel Drug Metabolism Reserve Physiotype to determine the metabolic capacity of a human individual. The Drug Metabolism Reserve Physiotype allows the determination of the innate metabolic capacity of the patient relevant to antidepressant and stimulant treatment and can be predicted and diagnosed simply from a blood sample. In the disclosed method, an individual is genotyped for a plurality of polymorphisms in a gene encoding CYP2C9, a gene encoding CYP2C19 and a gene encoding CYP2D6, and the genotypes are used to produce four novel indices, which relate to the metabolic capacity of the human individual.

1 Claim, 11 Drawing Sheets

PHYSIOGENOMIC METHOD FOR PREDICTING DRUG METABOLISM RESERVE FOR ANTIDEPRESSANTS AND STIMULANTS

CROSS-REFERENCE TO RELATED APPLICATIONS

This application is a nonprovisional of U.S. Provisional Application No. 61/254,767, filed Oct. 26, 2010, which is incorporated herein by reference in its entirety.

BACKGROUND

Major depressive disorder (MDD) is currently the leading cause of disability in North America as well as other countries and, according to the WHO, may become the second leading cause of disability worldwide (after heart disease) by the year 2020. Over the years, the elusive and highly variable nature of psychiatric disorders has led to drug therapy treatment that largely relies on empiricism to ascertain individual patient differences. This empirical approach has resulted in a high rate of refractory and adverse responses to drug therapies, rendering treatment of MDD one of the most significant challenges in psychiatry.

Both published literature studies and clinical experience reveal great variability in an individual's response to psychotropic drug treatment with regard to drug metabolism, side effects and efficacy. This variability is in part attributable to genetic differences that result in slowed or accelerated oxidation of many psychotropic drugs metabolized by the cytochrome P450 (CYP450) isoenzyme system in the liver. In particular, clinically relevant variants have been identified for the isoenzymes coded by the CYP2C9, CYP2C19 and CYP2D6 genes. Wile the pharmacogenetic significance of CYP2C9-deficient alleles is not as prominent in psychiatry as that of CYP2D6 and CYP2C19, it is known that the gene represents a minor metabolic pathway for some antidepressants. Therefore, polymorphisms in CYP2C9 may be important in psychiatric patients deficient for other CYP450 enzymatic activities. Some of the potential consequences of polymorphic drug metabolism are extended pharmacological effect, adverse drug reactions (ADRs), lack of prodrug activation, drug toxicity, increased or decreased effective dose, metabolism by alternative deleterious pathways and exacerbated drug-drug interactions. CYP450 isoenzymes are also involved in the metabolism of endogenous substrates, including neurotransmitter amines, and have been implicated in the pathophysiology of mood disorders. CYP2D6 activity has been associated with personality traits and CYP2C9 to MDD.

The CYP2D6 gene product metabolizes several antipsychotic (e.g., aripiprazole and risperidone) and antidepressants (e.g., duloxetine, paroxetine and venlafaxine). CYP2D6 is highly polymorphic. More than 60 alleles and more than 130 genetic variations have been described for this gene, located on chromosome 22q13. Clinically, the most significant phenotype is the null metabolizer, which has no CYP2D6 activity because it has two nonfunctional CYP2D6 alleles or is missing the gene altogether. The prevalence of null metabolizers is approximately 7% in Caucasians and 1-3% in other races. Gene duplications of CYP2D6 that may lead to an ultra-rapid metabolizer (UM) phenotype are also clinically significant. A recent worldwide study suggested that up to 40% of individuals in some North African and more than 20% in Australian populations are CYP2D6 UMs. In a 2006 US survey, the prevalence of CYP2D6 UMs was 1-2% in Caucasians and African-Americans. CYP2C9 is located on chromosome 10q24, and its gene product is involved in the metabolism of several important psychoactive substances (e.g., fluoxetine, phenytoin, sertraline and tetrahydrocannabinol). It has been reported that CYP2C9 activity is modulated by endogenous substrates such as adrenaline and serotonin. CYP2C19 is also located on chromosome 10q24, but in linkage equilibrium with CYP2C9. Its gene product is involved in the metabolism of various antidepressants (e.g., citalopram and escitalopram). For some psychotropics, a cumulative deficit in drug metabolism resulting from multigene polymorphisms in CYP2D6, CYP2C9 and CYP2C19 may be clinically significant. For example, gene products for CYP2C19 and CYP2D6 provide joint drug-metabolism pathways for various tricyclic antidepressants (e.g., amitriptyline and imipramine). Given that CYP2D6, CYP2C9 and CYP2C19 genes are not linked physically or genetically, their polymorphisms would be expected to segregate independently in populations.

Pharmacogenetics is a discipline that attempts to correlate specific gene variations with responses to particular drugs. Such DNA-guided pharmacotherapy would be potentially cost effective and could spare patients from unwanted side effects by matching each with the most suitable, individualized drug and dosing regimen at initiation of pharmacotherapy. There have been strategies personalizing dosing for psychiatric drugs according to algorithms derived from studies of blood levels. Beyond pharmacogenetics, it has become apparent that therapeutic index is a necessary concept in understanding how CYP450 polymorphism may influence personalized prescription.

A 1998 meta-analysis of 39 prospective studies in US hospitals estimated that 106,000 Americans die annually from ADRs. Adverse drug events are also common (50 per 1000 person years) among ambulatory patients, particularly the elderly on multiple medications. The 38% of events classified as 'serious' are also the most preventable. It is now clear that virtually every pathway of drug metabolism, transport and action is susceptible to gene variation. Within the top 200 selling prescription drugs, 59% of the 27 most frequently cited in ADR studies are metabolized by at least one enzyme known to have gene variants that code for reduced or nonfunctional proteins.

In psychiatry, the high carrier prevalence of deficient CYP450 alleles has significant implications for healthcare management. Uninformed prescribing of psychotropics to patients with highly compromised biochemical activity for the CYP450 isoenzymes, may expose 50% of patients to preventable severe side effects. If these patients were carriers of gene polymorphisms resulting in deficient psychotropic metabolism, their risk of adverse drug effects would substantially increase. Were DNA typing to be performed after development of drug resistance or intolerance, such information could guide subsequent pharmacotherapy and assist in diagnosing drug-induced side effects. The value of DNA typing for diagnosing severe drug side effects and treatment resistance has been documented in various case reports. Optimally, DNA typing could be performed prior to drug prescription in order to optimize therapy at the outset of psychotropic management.

While it is well known that interindividual variation in drug metabolism is highly dependent on inherited gene polymorphisms, the debate regarding the role of genotyping in clinical practice continues. The utility of the system described herein is to provide clinically relevant indices of drug metabolism status based on combinatorial genotypes of CYP2C9, CYP2C19 and CYP2D6. The combinatorial genotype so derived is termed the Drug Metabolism Reserve Physiotype.

SUMMARY

In one embodiment, a composition comprises, consists essentially of, or consists of a plurality of marker probes or amplification primers that detect or amplify a plurality of polymorphisms in a gene encoding CYP2C9 (SEQ ID NO:1), a gene encoding CYP2C19 (SEQ ID NO:2) and a gene encoding CYP2D6 (SEQ ID NO:3), comprising all of the following markers:

genotyping the individual to produce a combinatorial genotype, wherein the combinatorial genotype comprises both gene copies of each gene of the plurality of marker probes in the foregoing table;

calculating one or more index scores selected from the group consisting of the metabolic reserve index, the metabolic alteration index, the allele alteration index and the gene alteration index, based on the Table, wherein the metabolic reserve index, the metabolic alteration index, the allele alteration index are scored 0, 0.5, 1, 1.5 or 2 for each copy of each gene individually according to the Table, and the gene alteration index is scored 0 or 1 based on the combination of alleles for each marker, and all scores are added to produce the index score; and

| CYP2C9 | CYP2C19 | CYP2D6 | Metabolic Reserve | Metabolic Alteration | Allele Alteration |
|---|---|---|---|---|---|
| *1 | *1 | *1, *2 | 1 | 0 | 0 |
| *2 | | *9, *10, *17, *41 | 0.5 | 0.5 | 1 |
| | | *2a | 1.5 | 0.5 | 1 |
| | | *1XN, *2XN | 2 | 1 | 1 |
| *3, *4, *5, *6 | *2, *3, *4, *5, *6, *7, *8 | *3, *4, *6, *7, *8, *11, *12, *14, *15, *5, *4XN | 0 | 1 | 1 |

| CYP2C9 | CYP2C19 | CYP2D6 | Gene Alteration |
|---|---|---|---|
| *1*1 | *1*1 | *1*1, *1*2, *2*2 | 0 |
| All other allele combinations | All other allele combinations | All other allele combinations | 1 |

| Gene | Allele | Nucleotide Change |
|---|---|---|
| CYP2C9 | *1 | None |
| | *2 | 430C > T |
| | *3 | 1075A > C |
| | *4 | 1076T > C |
| | *5 | 1080C > G |
| | *6 | 818delA |
| CYP2C19 | *1 | None |
| | *2 | 681G > A |
| | *3 | 636G > A |
| | *4 | 1A > G |
| | *5 | 1297C > T |
| | *6 | 395G > A |
| | *7 | IVS5 + 2T > A |
| | *8 | 358T > C |
| CYP2D6 | *1 | None |
| | *1XN | Gene copy number (N) |
| | *2 | 1661G > C |
| | *2a | −1584C > G |
| | *2XN | Gene copy number (N) |
| | *3 | 2549delA |
| | *4 | 1846G > A |
| | *4XN | Gene copy number (N) |
| | *5 | Gene deletion |
| | *6 | 1707delT |
| | *7 | 2935A > C |
| | *8 | 1758G > T |
| | *9 | 2615_2617delAAG |
| | *10 | 100C > T |
| | *11 | 883G > C |
| | *12 | 124G > A |
| | *14 | 1758G > A |
| | *15 | 137_138InsT |
| | *17 | 1023C > T |
| | *41 | 2988G > A |

In another embodiment, a method of determining the metabolic capacity of a human individual relevant to antidepressant and stimulant treatment, comprises:

comparing the one or more index scores for the individual to a distribution of index scores for a population to determine the metabolic capacity of the human individual relevant to antidepressant and stimulant treatment.

DETAILED DESCRIPTION

Figure 1:
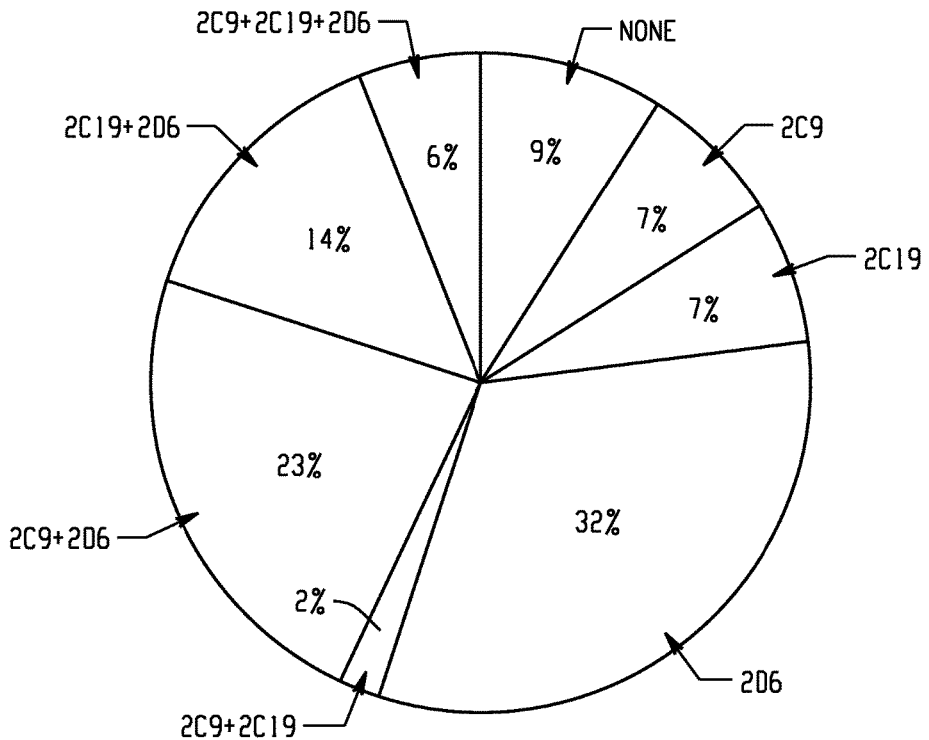
FIG. 1 shows the frequencies of polymorphisms across CYP2C9, CYP2C19 and CYP2D6 for 577 psychiatric patients.

Disclosed herein are compositions and methods relevant to a novel Drug Metabolism Reserve Physiotype to determine the metabolic capacity of a human individual. The Drug Metabolism Reserve Physiotype allows the determination of the innate metabolic capacity of the patient relevant to antidepressant and stimulant treatment and can be predicted and diagnosed simply from a blood sample. Patients intolerant to antidepressant and stimulant drugs or refractory to treatment can be tested for their drug metabolism capacity to benchmark their drug metabolism reserve by genotyping three genes, CYP2D6, CYP2C9, and CYP2C19, as described herein. Therapy can be directed to drugs whose primary metabolic pathway is least deficient or normal in an individual patient, thus markedly improving the safety and efficacy of pharmacotherapy.

The Drug Metabolism Reserve Physiotype assays a total of 34 alleles for CYP450 (Cytochrome P450) genes CYP2D6, CYP2C9, and CYP2C19. The corresponding hepatic isoenzymes metabolize widely utilized neuropsychiatric drugs. These isoenzymes are highly polymorphic in gene sequence and protein structure. Their resultant variable biochemical properties substantially alter individual patient drug response. Table 1 provides the 34 gene variants in the ensemble. In one embodiment, a composition comprises all of the markers in Table 1. In another embodiment, a composition consists essentially of the markers in Table 1. In yet another embodiment, a composition consists of the markers in Table 1.

TABLE 1

CYP450 variants

| Gene | Allele | Nucleotide Change | Effect |
|---|---|---|---|
| CYP2C9 | *1 | None | Wild-Type |
|  | *2 | 430C > T | R144C |
|  | *3 | 1075A > C | I359L |
|  | *4 | 1076T > C | I359T |
|  | *5 | 1080C > G | D360E |
|  | *6 | 818delA | Frame shift |
| CYP2C19 | *1 | None | Wild-Type |
|  | *2 | 681G > A | Splicing defect |
|  | *3 | 636G > A | W212X |
|  | *4 | 1A > G | GTG initiation codon |
|  | *5 | 1297C > T | R433W |
|  | *6 | 395G > A | R132Q |
|  | *7 | IVS5 + 2T > A | Splicing defect |
|  | *8 | 358T > C | W120R |
| CYP2D6 | *1 | None | Wild-Type |
|  | *1XN | Gene copy number (N) | Locus expanded |
|  | *2 | 1661G > C | None |
|  | *2a | −1584C > G | Promoter |
|  | *2XN | Gene copy number (N) | Locus expanded |
|  | *3 | 2549delA | Frameshift |
|  | *4 | 1846G > A | Splicing defect |
|  | *4XN | Gene copy number (N) | Locus expanded |
|  | *5 | Gene deletion | Locus deleted |
|  | *6 | 1707delT | Frameshift |
|  | *7 | 2935A > C | H324P |
|  | *8 | 1758G > T | G169X |
|  | *9 | 2615 2617delAAG | K281del |
|  | *10 | 100C > T | P34S |
|  | *11 | 883G > C | Splicing defect |
|  | *12 | 124G > A | G42R |
|  | *14 | 1758G > A | G169R |
|  | *15 | 137_138InsT | Frameshift |
|  | *17 | 1023C > T | T107I |
|  | *41 | 2988G > A | Splicing defect |

For each gene, allele *1 is also referred to as Wild-Type (WT)
CYP2C9 (SEQ ID NO: 1; Genbank accession no. NM_000771.3, NP_000762)
CYP2C19 (SEQ ID NO: 2; Genbank accession no. NM_000769, NP_000760)
CYP2D6 (SEQ ID NO: 3; Genbank accession no. NM_000106, NP_000097.2, isoform 1)

In order to determine the novel indices described herein, the types and carrier prevalences of Drug Metabolism Reserve Physiotypes in Major Depressive Disorder (MDD) patients were compared to a control group of non-psychiatrically ill, medical outpatients. The utility of the indices was confirmed through a case control study conducted using 73 psychiatric outpatients diagnosed with depression and referred to a tertiary center, The Institute of Living (Hartford, Conn. USA), for treatment resistance or intolerable side effects to psychotropic drugs. The controls were 120 cardiovascular patients from Hartford Hospital being treated for dyslipidemia but otherwise healthy and not psychiatrically ill. Within the psychiatric population, 57% of individuals were carriers of non wild-type alleles for 2-3 genes, compared to 36% in the control population (p<0.0001). The balance, 43% in the psychiatric population and 64% in the control, were carriers of non wild-type alleles for 0-1 genes.

In one embodiment, a method of determining the metabolic capacity of a human individual relevant to antidepressant and stimulant treatment includes determining both gene copies of each gene of the plurality of marker probes described herein in Table 1. The genotype is referred to as a combinatorial genotype as is it includes data for a combination of genes.

Once the genotype of the human individual has been determined, an index score for the human individual is produced based on the genotype, and the index score for the individual is then compared to a distribution of index scores for a population to predict the drug sensitivity for the human individual. In order to correlate quantitative values with an individual's Drug Metabolism Reserve Physiotype, a series of novel indices were constructed. The following are the four indices:

1. The Metabolic Reserve Index
2. The Metabolic Alteration Index
3. The Allele Alteration Index (Number of non-WT alleles)
4. The Gene Alteration Index (Number of non-WT gene loci)

All four indices assign a numeric value to CYP450 alleles depending on their altered phenotype. One, two, three or all four indices can be calculated for the individual and compared to the distribution of index scores for a population. Table 2 shows how phenotypes and special case alleles are scored in the four different indices. The first three listed indices result from the summation of both gene copies in the CYP2C9, CYP2C19 and CYP2D6 genes. The final index considers both alleles per gene when scoring the genotype, with only an entirely wild-type genotype receiving a score of "0" for that particular gene.

TABLE 2

| CYP2C9 | CYP2C19 | CYP2D6 | Metabolic Reserve | Metabolic Alteration | Allele Alteration |
|---|---|---|---|---|---|
| *1 | *1 | *1, *2 | 1 | 0 | 0 |
| *2 | | *9, *10, *17, *41 | 0.5 | 0.5 | 1 |
| | | *2a | 1.5 | 0.5 | 1 |
| | | *1XN, *2XN | 2 | 1 | 1 |
| *3, *4, *5, *6 | *2, *3, *4, *5, *6, *7, *8 | *3, *4, *6, *7, *8, *11, *12, *14, *15, *5, *4XN | 0 | 1 | 1 |

| CYP2C9 | CYP2C19 | CYP2D6 | Gene Alteration |
|---|---|---|---|
| *1*1 | *1*1 | *1*1, *1*2, *2*2 | 0 |
| All other allele combinations | All other allele combinations | All other allele combinations | 1 |

The Metabolic Reserve Index:

The metabolic reserve index is designed to represent a series of discrete CYP450 metabolic phenotypes from null (index=0) to ultra rapid (index>6). Since deficient and null alleles are scored lower than wild-type alleles, the lower the index the greater the metabolic deficiency. Similarly, as ultra-rapid alleles are scored higher than wild-type, the presence of these alleles contributes a greater value to the total metabolic index.

The Metabolic Alteration Index:

As shown in Table 1, the *1 allele in all three genes represents the wild-type phenotype and is associated with a normal metabolic capacity. The CYP2D6*2 allele is also considered to be wild-type. In this index, we capture any departure from wild-type alleles on any of the CYP2C9, CYP2C19 and CYP2D6 genes and score it according to the method in Table 3. Given that the wild-type allele is assigned a score of "0", any departure from wild-type, whether deficient or ultra-rapid is scored higher than zero as the index measures the absolute difference. More severe mutations are assigned a greater difference from the wild-type allele.

The Allele Alteration Index (Number of non-WT alleles):

This index depends on a binary scoring of each individual allele. In this case, the index represents the sum of each of the six alleles, designated as either wild-type (*1, CYP2D6*2) or non wild-type (all other alleles). Thus, a score of "0" denotes a patient who is wild-type across all three genes, while a score of "6" indicates a patient with two non wild-type alleles are all three genes.

The Gene Alteration Index (Number of non-WT gene Loci):

The gene alteration index was created to capture a broad overview of gene deficiencies, as opposed to allelic mutations. Like the allele alteration index, this scoring method utilizes binary scoring by scoring a gene carrying any non wild-type allele as "1" and a gene with two wild-type alleles as "0". Therefore, an individual with a score of "3" has at least one non wild-type allele on all three genes, while an individual with a score of "0" has no mutant alleles.

The calculated index scores for the individual are then compared to a distribution of index scores for a population to determine the metabolic capacity of the human individual relevant to antidepressant and stimulant treatment.

In one embodiment, comparing the scores for the individual to a population is done using a metabolic ranking curve. The metabolic ranking curves were derived using the same formula for all indices.

J=number of levels in index (length of N)
N=array of counts per index level
x=individual index value $$\frac{\sum_{\{i|x_i<x\}} N_i + \frac{1}{2} \sum_{\{i|x_i=x\}} N_i}{\sum_{i=1}^{j} N_i}$$

For instance, for an individual with a score of 5 on the metabolic reserve index:
j=11
N=[1, 6, 15, 23, 61, 84, 156, 96, 84, 37, 14]
x=5
Whereas a score of 2 on the metabolic alteration index:
j=9
N=[49, 79, 170, 118, 84, 39, 27, 18, 1]
x=2

The metabolic ranking curve calculates an individual's position (0 to 100%) for a particular Drug Metabolism Reserve Physiotype index. This curve uses the distribution of the 577 psychiatric subjects as a model to determine where an individual fits in the index's distribution. Such a placement will provide a clinician with a clearer comparative concept of his/her patient's metabolic status in relation to the "average" (50%) individual. In conjunction with the raw index score, the physician will now have a better understanding of a patient's absolute metabolic ability in addition to their metabolic ability in relation to the sample population.

In one embodiment, the human individual is a psychiatric patient such as a patient diagnosed with depression. In another embodiment, the patient is a patient with major depressive disorder. In yet another embodiment, the patient with major depressive disorder has been hospitalized for the major depressive disorder.

In another embodiment, the method further comprises customizing a drug regimen for the psychiatric patient guided by the Drug Metabolism Reserve Physiotype. This guidance will be achieved by evaluating relative contributions to Drug Metabolism Reserve Physiotype index values and rankings on a gene-by-gene basis, considering CYP2C9, CYP2C19 and CYP2D6. Gene-specific index values associated with substantially decreased metabolic reserve, or greatly increased metabolic alteration will lead to recommendations to avoid those drugs which are a substrate of the isoenzymes coded by the altered gene(s). An additional warning will be provided if this altered isoenzyme constitutes the primary or sole metabolic pathway for that drug. Moderately decreased metabolic reserve or moderately increased metabolic alteration will prompt a warning to consider an altered dose and monitor with caution those drugs that are a substrate of the altered isoenzymes. If a given gene's relative contribution to the index values and ranking indicates that the respective isoenzyme is functional, drugs metabolized primarily by that isoenzyme will be recommended to the physician. If the CYP2D6 index contribution value is determined to indicate ultra-rapid metabolism, the physician will be notified that a normal dose may prove ineffective and that there is an increased risk for drug-interactions if the patient is prescribed a pro-drug metabolized by CYP2D6 isoenzyme. In summary, the proportional contribution of each gene to the Drug Metabolism Reserve Physiotype indices will be used to guide physicians to choose appropriate medications for their patients, which are metabolized primarily by isoenzymes for which the patient has the most metabolic reserve and least metabolic alteration.

In yet another embodiment, the method further comprises correlating the one or more index scores for the individual with a predicted length of hospitalization. The method further optionally comprises customizing a drug regimen for the patient to reduce a length of hospitalization or reduce a risk of re-hospitalization. By providing pharmacogenetic guidance to physicians as described above, patients with lower metabolic reserve (associated with longer hospitalization) will receive treatment regimens appropriate for their individual metabolic capacities. Based on our evidence, we predict that this guidance will lead to more efficient and effective treatment decisions, less adverse drug reactions and therefore shorter hospitalizations.

In one embodiment, the index score is for the gene alteration index. The inventors herein have unexpectedly discovered that the gene alteration index score can be correlated with a new syndrome called Drug Sensitivity Syndrome. When the gene alteration index score is equal to 3 and the individual is diagnosed with Drug Sensitivity Syndrome.

Aspects of the method described herein may be embodied as a system, or computer program product. Accordingly, aspects may take the form of an entirely hardware embodiment, an entirely software embodiment or an embodiment combining software and hardware aspects that may all generally be referred to herein as a "circuit," "module" or "system." Furthermore, aspects may take the form of a computer program product embodied in one or more computer readable medium(s) having computer readable program code embodied thereon. The computer readable medium may be a computer readable signal medium or a computer readable storage medium. A computer readable storage medium is, for example, but not limited to, an electronic, magnetic, optical, electromagnetic, infrared, or semiconductor system, apparatus, or device, or any suitable combination of the foregoing. In addition, computer program code for carrying out operations for aspects of the method disclosed herein may be written in a combination of one or more programming languages. The program code may execute entirely on the user's computer, partly on the user's computer, as a stand-alone software package, partly on the user's computer and partly on a remote computer or entirely on the remote computer or server. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The invention is further illustrated by the following non-limiting examples:

Example 1

Drug Metabolism Reserve Physiotype Indices with 577 Patient Blood Samples

Sample collection: 577 blood samples were collected over a period of 4 years and 3 months beginning in July of 2005. 422 patient samples were referred to the Laboratory of Personalized Health at Genomas for CYP450 diagnostic genotyping as part of their clinical care because of efficacy or safety problems related to their medications. 150 samples came as part of a collaborative study with The Institute of Living at Hartford Hospital.

Patient cohorts: Of the 577 patients 57% are female and 43% are male. Patient date of birth was available for 572 and the average patient age was 37.47 years old as of Sep. 29, 2009. No ethnic data yet.

Single Nucleotide Polymorphism (SNP) assays: CYP450 DNA typing data were obtained for all 577 patients on CYP2C9, CYP2C19 and CYP2D6. Blood samples were collected into tubes containing either EDTA or citrate and were extracted from lymphocytes using the Qiagen EZ-1 robotic DNA isolation procedure. DNA typing was performed at the Genomas Laboratory of Personalized Health (LPH) at Hartford Hospital. LPH is a high-complexity clinical DNA testing center licensed by the Connecticut Department of Public Health (CL-0644) and certified by the Centers for Medicare and Medicaid Services (ID #07D1036625) under CLIA (Clinical Laboratory Improvement Amendments).

TAG-ITT™ Mutation Detection assays (Luminex Corporation, Austin Tex.) were utilized for DNA typing of 6, 8, and 20 alleles in genes CYP2C9, CYP2C19, and CYP2D6, respectively. These assays employed Polymerase Chain Reaction (PCR) to amplify selectively the desired gene without co-amplifying pseudogenes or other closely related sequences. In addition, the assay employs a PCR strategy to amplify fragments characteristic of unique genomic rearrangements in order to detect the presence of the deletion and duplication alleles in these genes. The assays use multiplexed Allele Specific Primer Extension (ASPE) to identify small nucleotide variations including single base changes and deletions of one or 3 bases on the LUMINEX xMAP™ system (Luminex Corporation, Austin Tex.).

Allele categorization: We classified the alleles into clinically distinct categories for each of the three genes examined as null, deficient, functional, or ultra based on well-defined molecular properties of the altered gene. Null alleles lack any enzymatic activity because the altered gene does not produce a functional protein. Such null alleles include gene deletions, frame shift mutations, stop codons, and splicing defects. Deficient alleles have sub-functional enzymatic activity due to nucleotide substitutions resulting in amino acid changes in the protein, and these variants may manifest sub-normal enzymatic activity for some drug substrates. The functional allele refers to the genetic "wild-type", the most common allele in the population with enzymatic activity considered normal. Ultra alleles exhibit increased enzymatic activity as a consequence of either gene duplication or a promoter change. Table 1 lists alleles detected in this patient cohort and their functional classification. To determine the combinatorial non wild-type frequency across all three genes examined, we used the genotype data for each patient in each population and tallied the number of subjects who had variant alleles in 3, 2, 1 or no genes.

Conventions for naming the alleles according to the Human Cytochrome P450 (CYP) Allele Nomenclature Committee have been followed in this research. Accordingly, all variant alleles contain nucleotide changes that have been shown to affect transcription, splicing, translation, posttranscriptional or posttranslational modifications, result in at least one amino acid change or alter the genomic structure of the chromosome locus by gene expansion or deletion.

Results: Among psychiatric patients, results from the LPH show a significant prevalence of carriers of altered combinatorial genotypes for CYP2C9, CYP2C19 and CYP2D6 genes. FIG. 1 shows the frequencies of polymorphisms across multiple genes. Of the 577 patients genotyped, 49 were wild-type for CYP2C9, CYP2C19 and CYP2D6. 265 (47%) were polymorphic on only one of the three genes. Of those 265, individuals with mutations on the CYP2D6 gene accounted for 186. Patients with polymorphisms across two of the three genes made up 39% of the population (227 individuals). Finally, 6% (36) samples had at least one non wild-type allele in all three genes tested. These results are also displayed as a histogram in FIG. 5 and correlate directly with the Gene Alteration Index.

Figure 2:
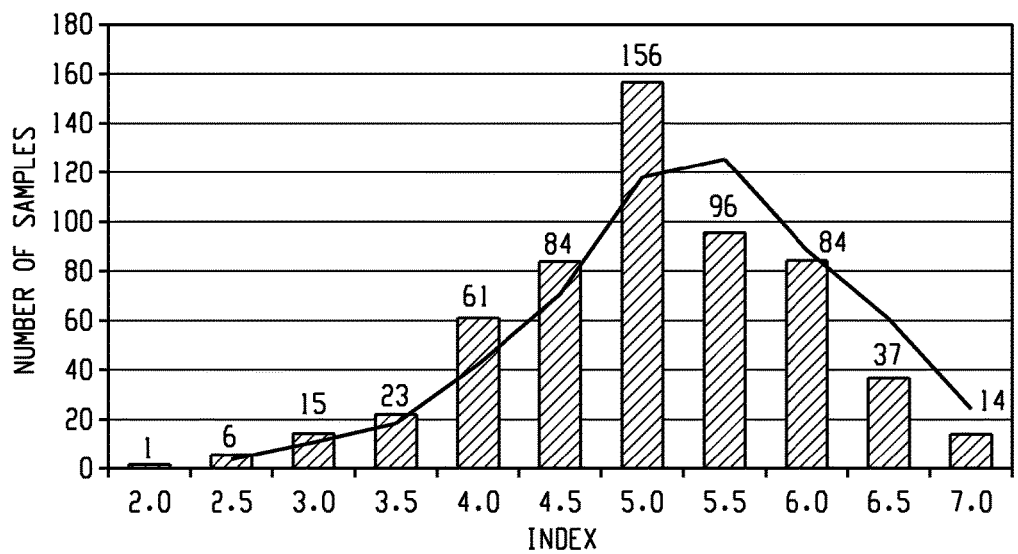
FIG. 2 shows the histogram for the Metabolic Reserve Index for 577 psychiatric patients.
Figure 3:
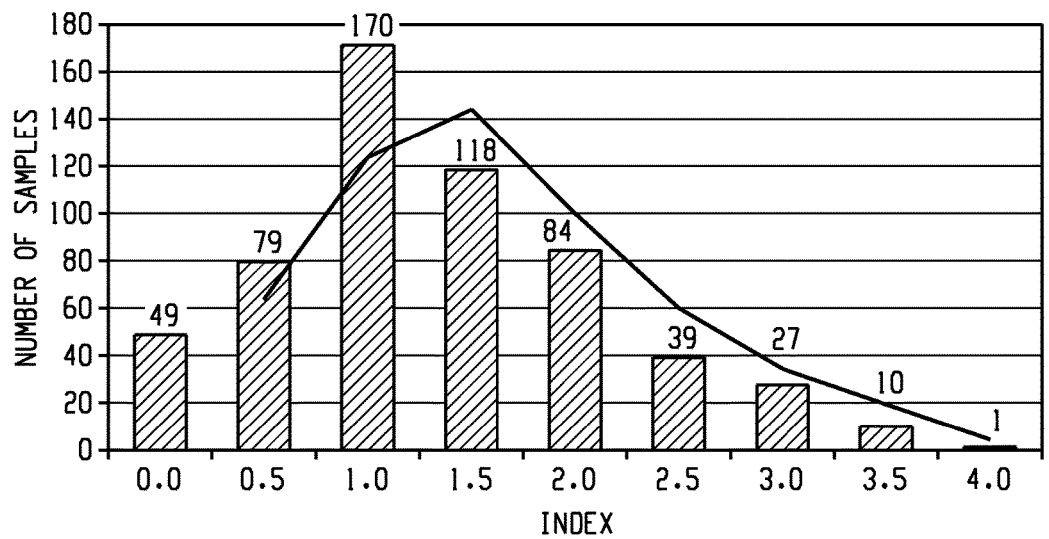
FIG. 3 shows the histogram for the Metabolic alteration index for 577 psychiatric patients.
Figure 4:
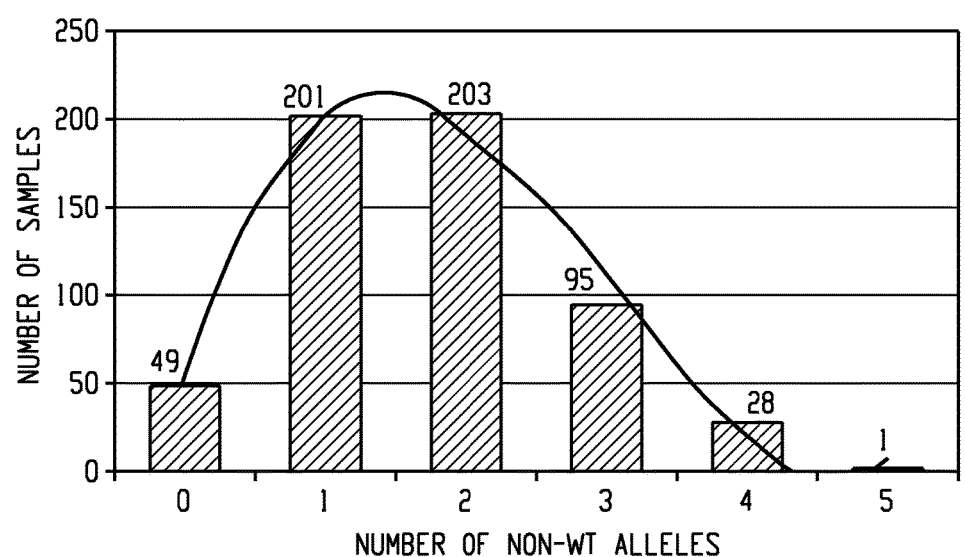
FIG. 4 shows the histogram for the Allele Alteration Index for 577 psychiatric patients.
Figure 5:
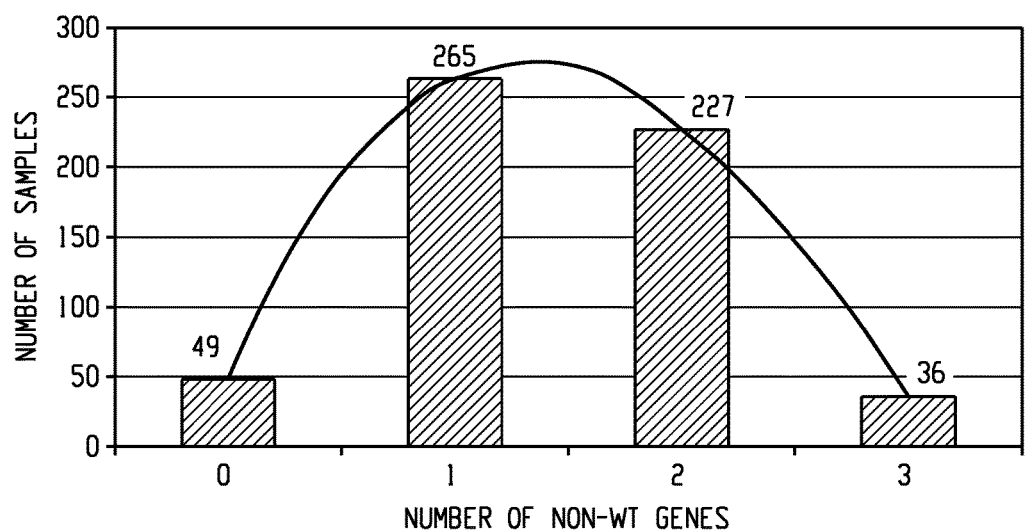
FIG. 5 shows the histogram for the Gene Alteration Index for 577 psychiatric patients.

FIGS. 2-5 are histograms of the 577 psychiatric patients that depict the distributions and counts for each Drug Metabolism Reserve Physiotype index, calculated in accordance with Table 2. FIG. 2 shows the histogram for the Metabolic reserve index. The median index value is 5.0 and the upper-boundaries for the $1^{st}$ and $3^{rd}$ quartiles are 4.5 and 5.5, respectively. FIG. 3 is the Allele Alteration Index histogram. In this data set, the median value is 1.0 and the $1^{st}$ and $3^{rd}$ quartile boundaries are 1.0 and 2.0, respectively. The median values in FIG. 4 and FIG. 5 are 2.0 and 1.0, respectively.

Figure 6:
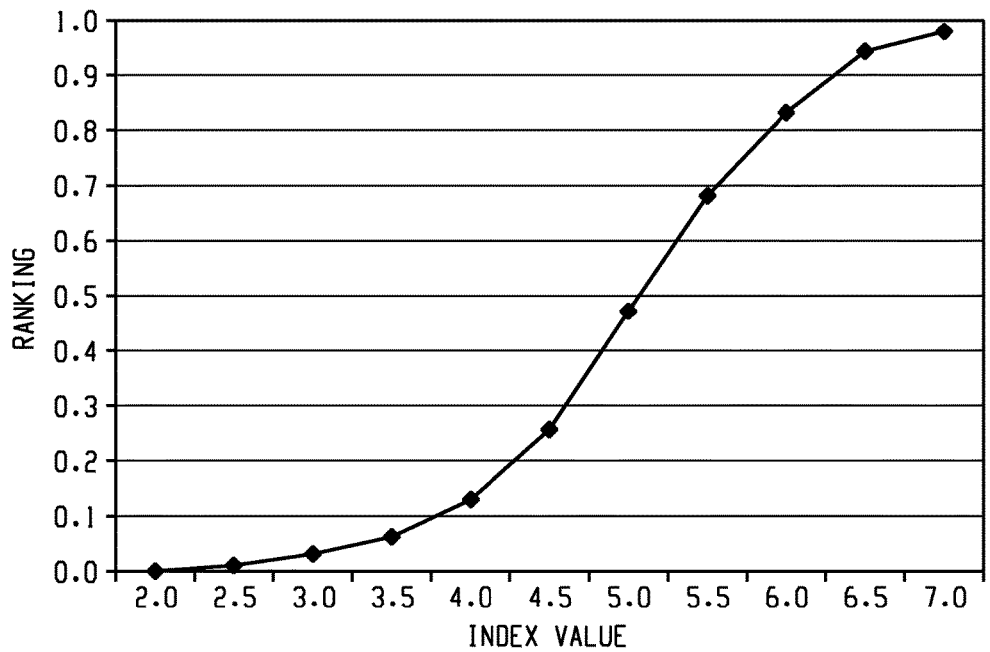
FIG. 6 shows the metabolic curve for the Metabolic Reserve Index for 577 psychiatric patients.
Figure 7:
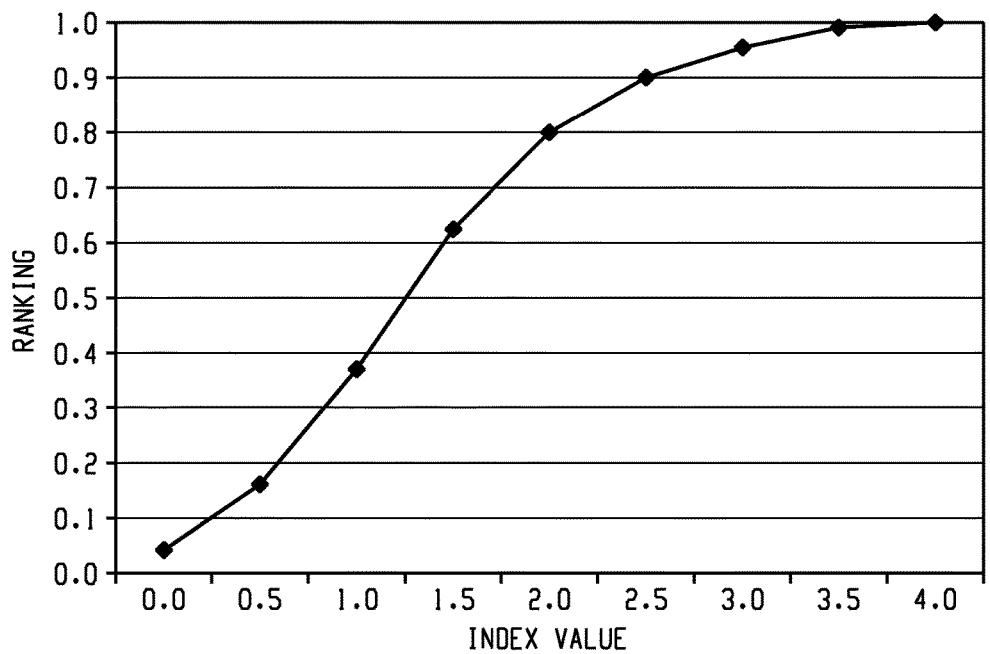
FIG. 7 shows the metabolic curve for the Metabolic alteration index for 577 psychiatric patients.
Figure 8:
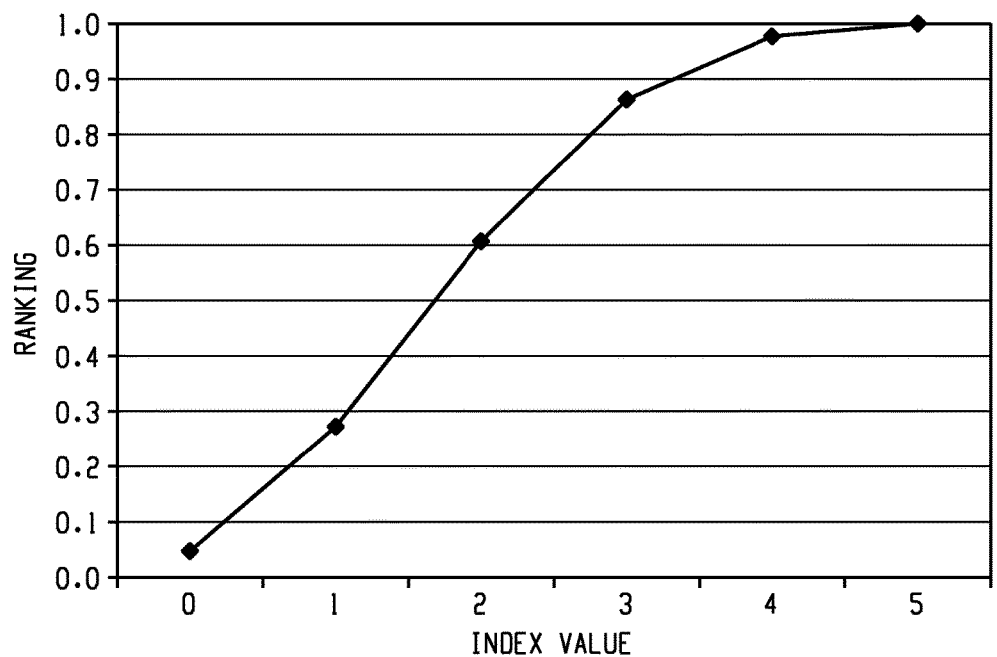
FIG. 8 shows the metabolic curve for the Allele Alteration Index for 577 psychiatric patients.
Figure 9:
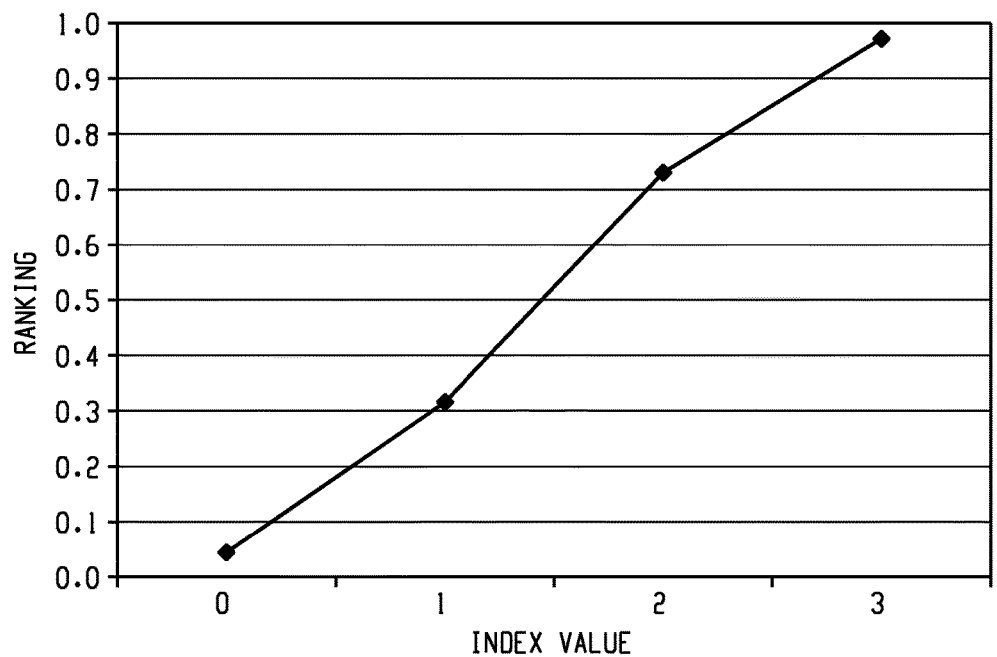
FIG. 9 shows the metabolic curve for the Gene Alteration Index for 577 psychiatric patients.

In each index, the median value correlates to the 50% value of the metabolic curve. An example of the metabolic curve for the Metabolic reserve index is shown in FIG. 6, the Metabolic alteration index in FIG. 7, and the Allele Alteration Index in FIG. 8 and the Gene Alteration Index in FIG. 9.

Ten individuals were chosen to demonstrate in detail the process to derive Drug Metabolism Reserve Physiotype indices and metabolic ranking calculations. See Table 3 for metabolic ranking calculation and Table 4 for Drug Metabolism Reserve Physiotype index calculation. Table 3 outlines the data used to calculate the rankings associated with each discrete metabolic index value. In addition, the variable values used in the metabolic ranking formula are outlined at the bottom of each index column. The variable value "x" denotes the variable index value for a particular individual dependent on their Drug Metabolism Reserve Physiotype. The calculation of these index values is outlined in Table 4. For each index, the values assigned to each allele in each gene are enumerated. The two allele values are separated with a semicolon (e.g. 0.5; 1 for allele1; allele2). The sum of the allele values represents the index value for that given genotype. That index value is then assigned to the "x" variable in the metabolic ranking formula to determine the relative metabolic position on the ranking curve. This can be visualized by locating the index value on the X-axis of the distribution represented in FIGS. 6-9 and noting the corresponding localization on the metabolic curve itself.

TABLE 3

| Metabolic Reserve | | | Metabolic Alteration | | | Allele Alteration | | | Gene Alteration | | |
|---|---|---|---|---|---|---|---|---|---|---|---|
| Index value | N | Ranking | Index value | N | Ranking | Index value | N | Ranking | Index value | N | Ranking |
| 2 | 1 | 0.00 | 0 | 49 | 0.04 | 0 | 49 | 0.04 | 0 | 49 | 0.04 |
| 2.5 | 6 | 0.01 | 0.5 | 79 | 0.15 | 1 | 201 | 0.26 | 1 | 265 | 0.31 |
| 3 | 15 | 0.03 | 1 | 170 | 0.37 | 2 | 203 | 0.61 | 2 | 227 | 0.74 |
| 3.5 | 23 | 0.06 | 1.5 | 118 | 0.62 | 3 | 95 | 0.87 | 3 | 36 | 0.97 |
| 4 | 61 | 0.13 | 2 | 84 | 0.79 | 4 | 28 | 0.97 | | | |
| 4.5 | 84 | 0.26 | 2.5 | 39 | 0.90 | 5 | 1 | 1.00 | | | |
| 5 | 156 | 0.46 | 3 | 27 | 0.96 | | | | | | |
| 5.5 | 96 | 0.68 | 3.5 | 10 | 0.99 | | | | | | |
| 6 | 84 | 0.84 | 4 | 1 | 1.00 | | | | | | |
| 6.5 | 37 | 0.94 | | | | | | | | | |
| 7 | 14 | 0.99 | | | | | | | | | |

RANKING EQUATION VARIABLES:

| j = 11 | j = 9 | j = 6 | j = 4 |
|---|---|---|---|
| x = index value | x = index value | x = index value | x = index value |
| N = Array(N column) | N = Array(N column) | N = Array(N column) | N = Array(N column) |

TABLE 4

| Genotypes | | | Metabolic Reserve | | | | | Metabolic Alteration | | | | |
|---|---|---|---|---|---|---|---|---|---|---|---|---|
| 2C9 | 2C19 | 2D6 | C9 | C19 | D6 | Sum | Rank | C9 | C19 | D6 | Sum | Rank |
| *2*3 | *1*1 | *1*1 | 0.5; 0 | 1; 1 | 1; 1 | 4.5 | 0.26 | 0.5; 1 | 0; 0 | 0; 0 | 1.5 | 0.62 |
| *1*1 | *1*1 | *1*1 | 1; 1 | 1; 1 | 1; 1 | 6 | 0.84 | 0; 0 | 0; 0 | 0; 0 | 0 | 0.04 |
| *1*3 | *1*2 | *6*6 | 1; 0 | 1; 0 | 0; 0 | 2 | 0.00 | 0; 1 | 0; 1 | 1; 1 | 4 | 1.00 |
| *1*1 | *1*2 | *10*2a | 1; 1 | 1; 0 | 0.5; 1.5 | 5 | 0.46 | 0; 0 | 0; 1 | 0.5; 0.5 | 2 | 0.79 |
| *1*1 | *1*1 | *1Dup*2a | 1; 1 | 1; 1 | 1; 2 | 7 | 0.99 | 0; 0 | 0; 0 | 0; 1 | 1 | 0.37 |
| *1*2 | *2*4 | *17*2a | 1; 0.5 | 0; 0 | 0.5; 1.5 | 3.5 | 0.06 | 0; 0.5 | 1; 1 | 0.5; 0.5 | 3.5 | 0.99 |

TABLE 4-continued

| | | | | | | | | | | | | | |
|---|---|---|---|---|---|---|---|---|---|---|---|---|---|
| *1*1 | *2*2 | *2a*2a | 1; 1 | 0; 0 | 1.5; 1.5 | 5 | 0.46 | 0; 0 | 1; 1 | 0.5; 0.5 | 2 | 0.79 |
| *1*3 | *1*1 | *1Dup*4 | 1; 0 | 1; 1 | 1; 0 | 4 | 0.13 | 0; 1 | 0; 0 | 0; 1 | 2 | 0.79 |
| *1*1 | *1*1 | *4*2 | 1; 1 | 1; 1 | 0; 1 | 5 | 0.46 | 0; 0 | 0; 0 | 1; 0 | 1 | 0.37 |
| *1*3 | *1*1 | Del*4 | 1; 0 | 1; 1 | 0; 0 | 3 | 0.03 | 0; 1 | 0; 0 | 1; 1 | 3 | 0.96 |

| Genotypes | | | Allele Alteration | | | | | Gene Alteration | | | | |
|---|---|---|---|---|---|---|---|---|---|---|---|---|
| 2C9 | 2C19 | 2D6 | C9 | C19 | D6 | Sum | Rank | C9 | C19 | D6 | Sum | Rank |
| *2*3 | *1*1 | *1*1 | 1; 1 | 0; 0 | 0; 0 | 2 | 0.61 | 1 | 0 | 0 | 1 | 0.31 |
| *1*1 | *1*1 | *1*1 | 0; 0 | 0; 0 | 0; 0 | 0 | 0.04 | 0 | 0 | 0 | 0 | 0.04 |
| *1*3 | *1*2 | *6*6 | 0; 1 | 0; 1 | 1; 1 | 4 | 0.97 | 1 | 1 | 1 | 3 | 0.97 |
| *1*1 | *1*2 | *10*2a | 0; 0 | 0; 1 | 1; 1 | 3 | 0.87 | 0 | 1 | 1 | 2 | 0.74 |
| *1*1 | *1*1 | *1Dup*2a | 0; 0 | 0; 0 | 0; 1 | 1 | 0.26 | 0 | 0 | 1 | 1 | 0.31 |
| *1*2 | *2*4 | *17*2a | 0; 1 | 1; 1 | 1; 1 | 5 | 1.00 | 1 | 1 | 1 | 3 | 0.97 |
| *1*1 | *2*2 | *2a*2a | 0; 0 | 1; 1 | 1; 1 | 4 | 0.97 | 0 | 1 | 1 | 2 | 0.74 |
| *1*3 | *1*1 | *1Dup*4 | 0; 1 | 0; 0 | 0; 1 | 2 | 0.61 | 1 | 0 | 1 | 2 | 0.74 |
| *1*1 | *1*1 | *4*2 | 0; 0 | 0; 0 | 1; 0 | 1 | 0.26 | 0 | 0 | 1 | 1 | 0.31 |
| *1*3 | *1*1 | Del*4 | 0; 1 | 0; 0 | 1; 1 | 3 | 0.87 | 1 | 0 | 1 | 2 | 0.74 |

Clinical Correlations of Drug Metabolism Reserve Physiotypes

Example 2

Clinical Correlation: LPH/IOL vs. Cardiology

For purposes of comparison, a second cohort of 92 cardiovascular patients treated with statins at Hartford Hospital was analyzed using the same four Drug Metabolism Reserve Physiotype indices. Unlike the primary population (N=577), which is comprised of 577 patients being treated for major depressive disorder (MDD) and/or other psychiatric conditions, this cohort consists of cardiology patients and thus acts as a suitable control population. In juxtaposing the metabolic index histograms of the two groups we find that these two cohorts have distinct metabolic profiles. FIGS. 10-13 show these charts.

Figure 10:
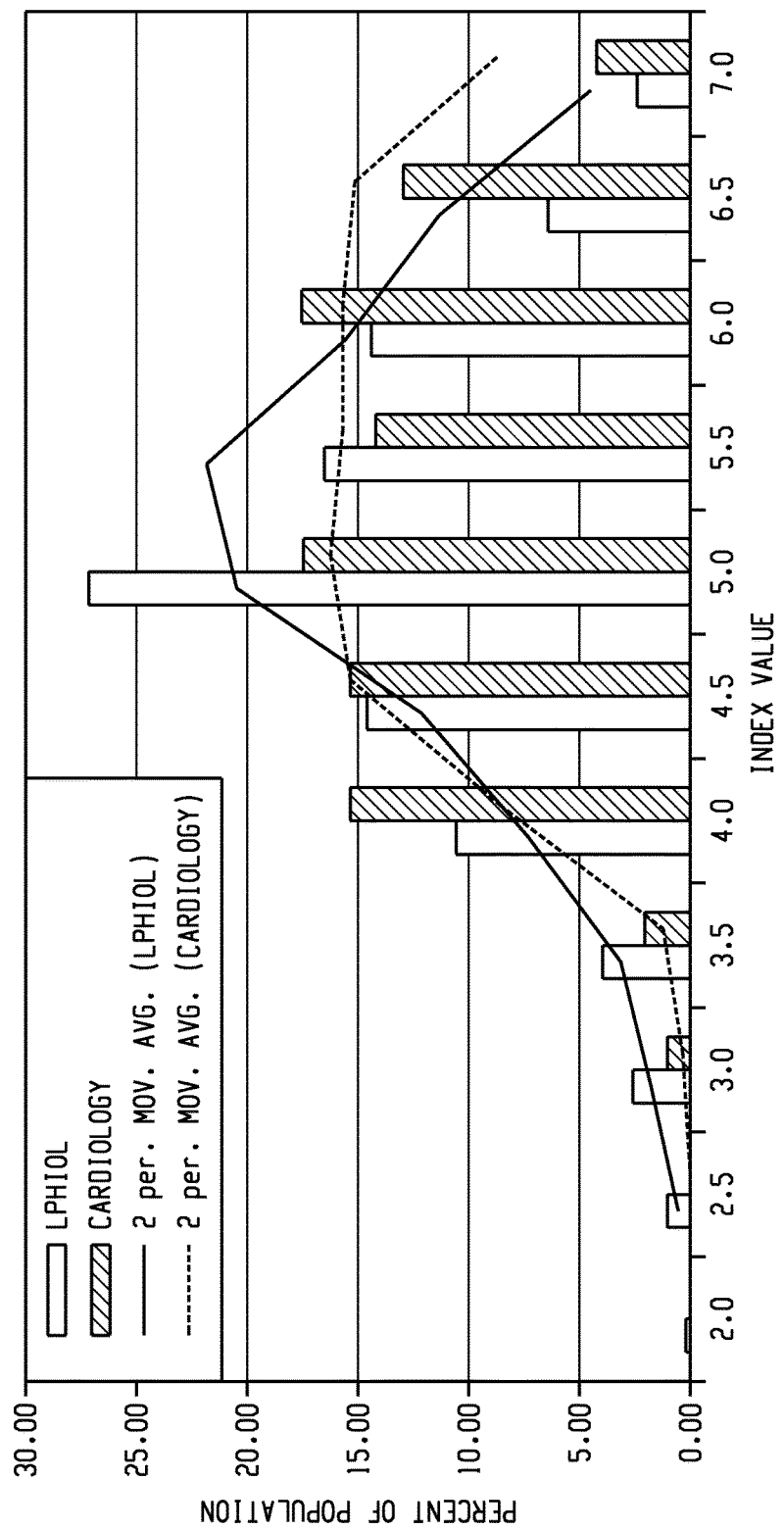
FIG. 10 shows the histogram by percentage for the Metabolic Reserve Index for 92 cardiovascular patients and 577 psychiatric patients.
Figure 11:
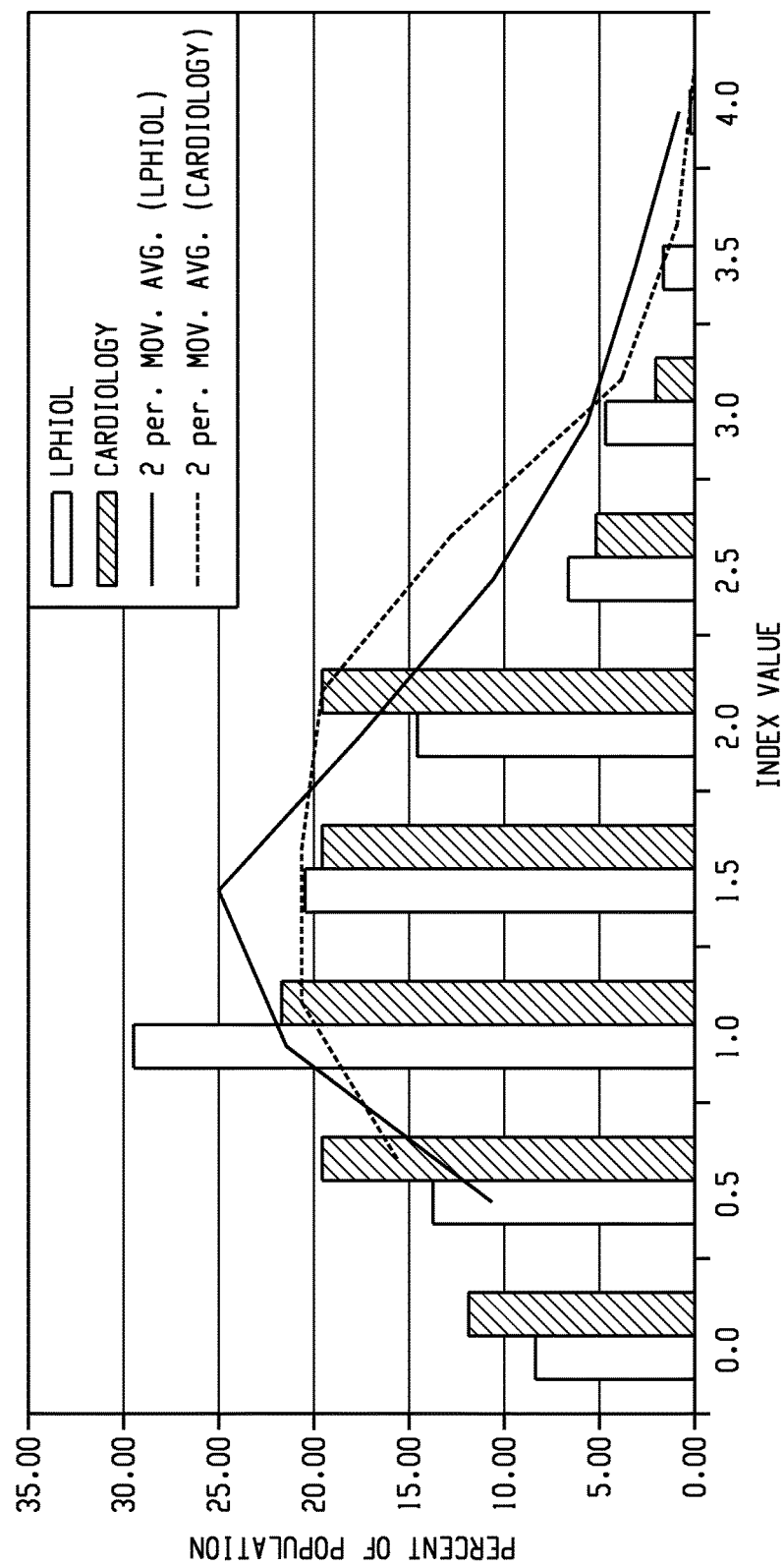
FIG. 11 shows the histogram by percentage for the Metabolic alteration index for 92 cardiovascular patients and 577 psychiatric patients.

Metabolic Reserve Index:

When comparing the mean index value of the psychiatric and control cohorts, it was found that the psychiatric population had a lower metabolic reserve than the control group (5.05 vs. 5.25, p=0.073). The median ranking of the control group was similarly elevated at 47% compared to 43%. FIG. 10 depicts the overlay of the histograms for the metabolic reserve index. The cardiovascular cohort seems more heterogeneous, with a smaller percentage of highly deficient individuals but a greater proportion of ultra-rapid metabolizers.

Metabolic Alteration Index:

Similarly, the metabolic alteration index shows a trend towards a greater departure from WT metabolic phenotype for the psychiatric population as compared to the control cohort (1.34 vs. 1.20, p=0.118). FIG. 11 again shows the control cohort to be more homogeneous, while containing a greater fraction of the wild-type and mildly-deficient individuals and less of the more severe metabolic phenotypes.

Figure 12:
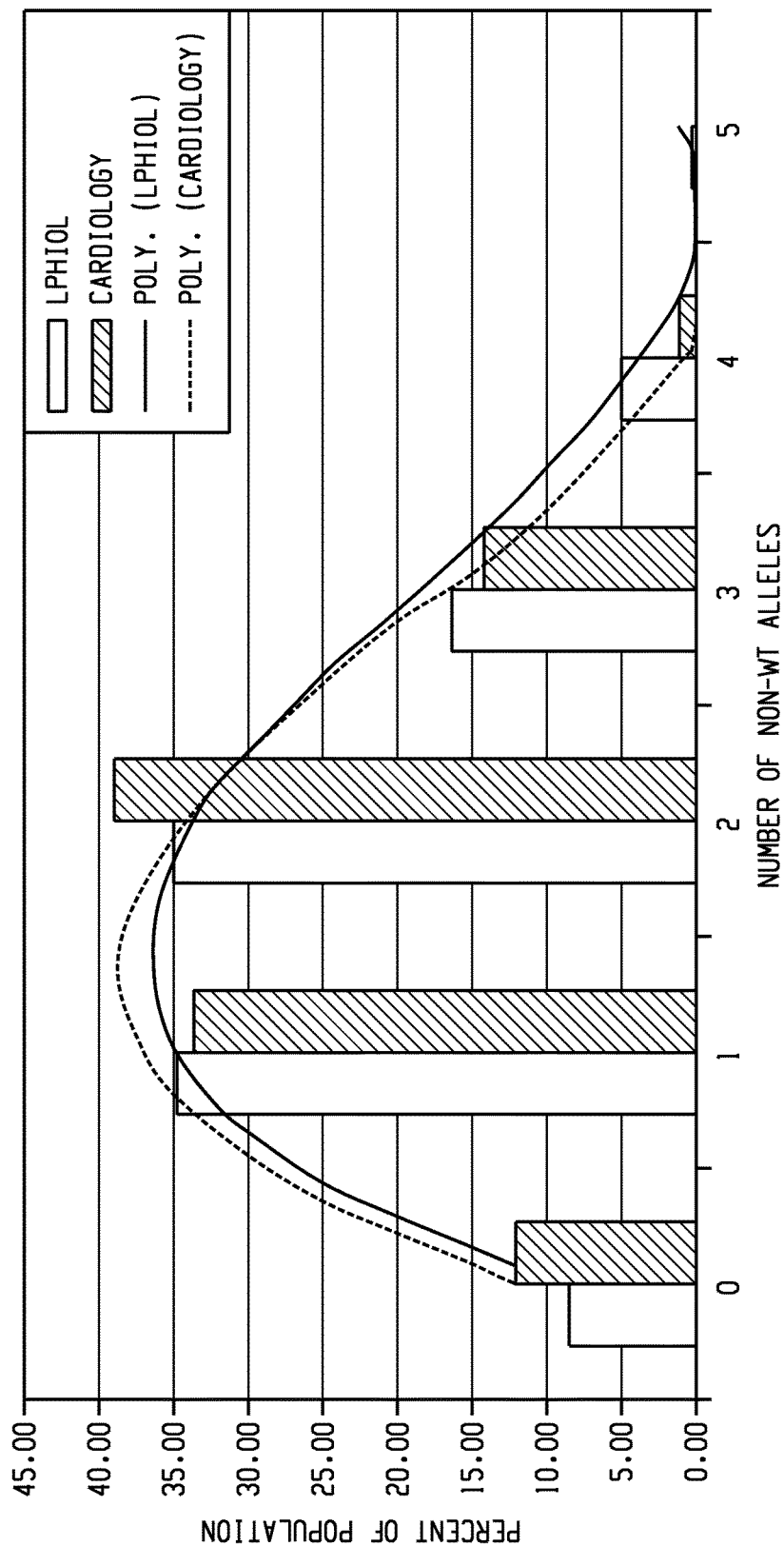
FIG. 12 shows the histogram by percentage for the Allele Alteration Index for 92 cardiovascular patients and 577 psychiatric patients.

Allele Alteration Index:

In accordance with the results from the above comparison, patients taking statins have less variant alleles than those taking psychiatric medications (1.59 vs. 1.75, p=0.123). FIG. 12 shows that the most striking differences are found, once again, in those individuals on the extremity of the curve, i.e. those with the greatest number of non-WT alleles.

Figure 13:
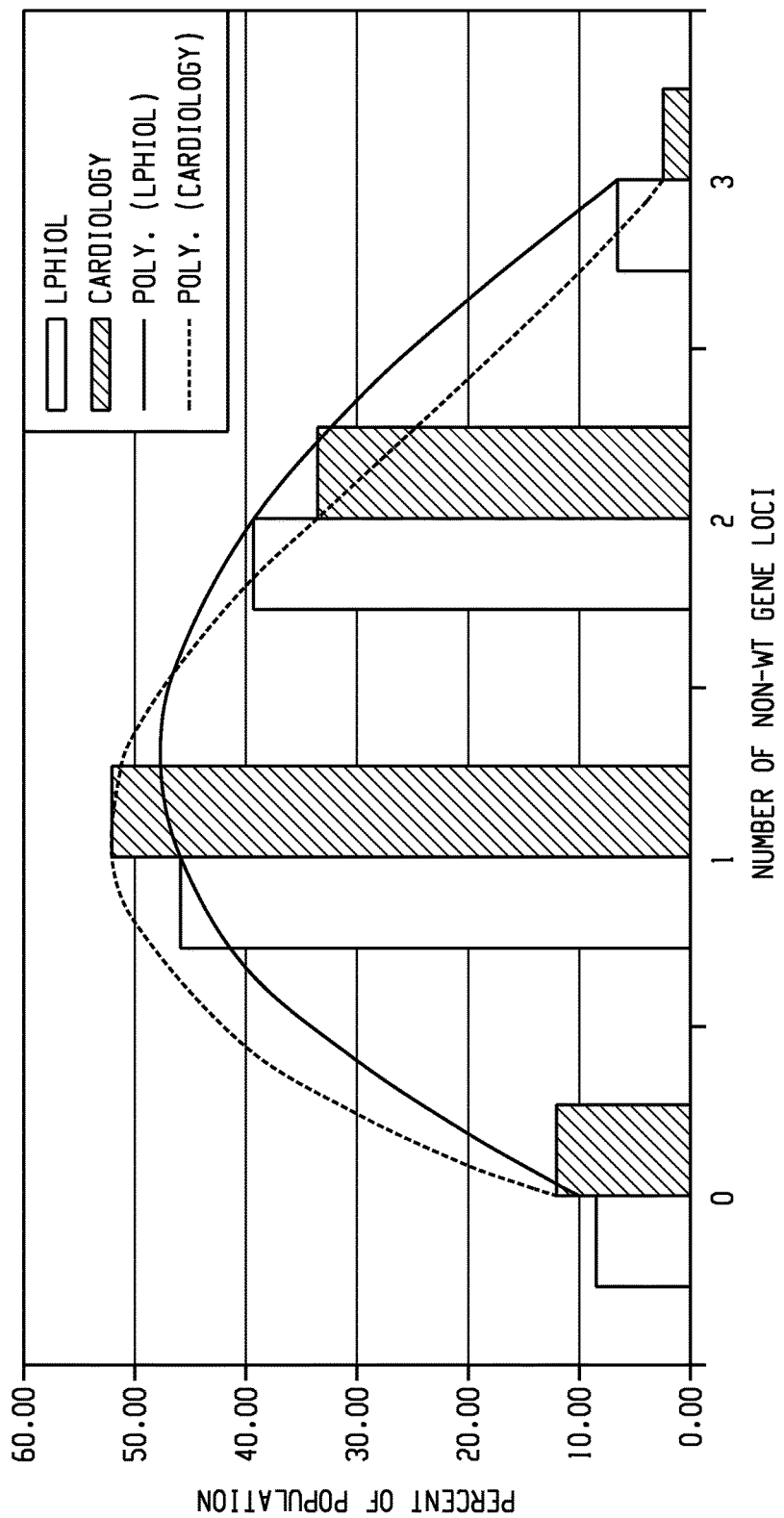
FIG. 13 shows the histogram by percentage for the Gene Alteration Index for 92 cardiovascular patients and 577 psychiatric patients.

Gene Alteration Index:

Analyzing the differences between the two groups at the level of gene alteration reveals the most significant differences in the populations. Psychiatric patients have an average of 1.43 non-WT genes while control patients have an average of 1.26 non-WT genes; p=0.030. FIG. 13 demonstrates that the psychiatric population has a lesser proportion of patients with 0-1 non-WT genes, but a greater fraction of individuals with 2-3 non-WT genes when compared with the cardiology control cohort.

The increased prevalence of drug metabolism alterations revealed by the Drug Metabolism Reserve Physiotype indices in the psychiatric cohort highlights its utility in elucidating inter-individual variation in this particular population. The purpose of the Drug Metabolism Reserve Physiotype indices is precisely to identify those individuals on the extremes of a normally distributed metabolic curve. FIGS. 10-13 illustrate this phenomenon clearly; the trend-lines matching models to the dataset reveal that the LPH-IOL cohort consistently has a greater proportion of individuals on the extremities of each index, (with the exception of ultra-rapid metabolizers in the metabolic reserve index). The index and ranking system described herein, together, would provide a physician with the absolute and relative placement of an individual patient on the metabolic spectrum, guiding treatment decisions in this highly variable genetic environment.

Example 3

IOL Referred Outpatients vs. Cardiology Control

A subset of the LPH/IOL cohort consists of 73 individuals evidencing severe problems with drug therapy in a community, requiring referral to IOL. This group is distinct from the LPH/IOL population in that their negative response to psychotropic drug therapy was more severe than the average patient in the larger IOL/LPH cohort. They were referred to the Laboratory of Personalized health due to these increased adverse reactions or lack of efficacy. In this cohort, the majority of psychiatric patients (57/73) were taking two or more psychotropic medications at the time of the study.

In all cases, their average Drug Metabolism Reserve Physiotype index values depart from the control cohort's to a greater degree than the larger IOL/LPH group. Regarding the Metabolic Reserve Index, the outpatient cohort had an average reserve of 4.95 compared to 5.25 for the cardiology control group (p=0.048). In the Metabolic Alteration Index, the average alteration was 1.44 and 1.20 for the outpatient and control groups, respectively (p=0.060). The psychiatric outpatient subgroup has an average of 1.90 non wild-type alleles whereas the control population has an average of 1.59 non wild-type alleles (p=0.048) corresponding to the Allele Alteration Index. Finally, the outpatient group has 1.60 non wild-type genes on average, compared to a mean value of 1.26 non wild-type genes for the control group (p=0.004).

Figure 14:
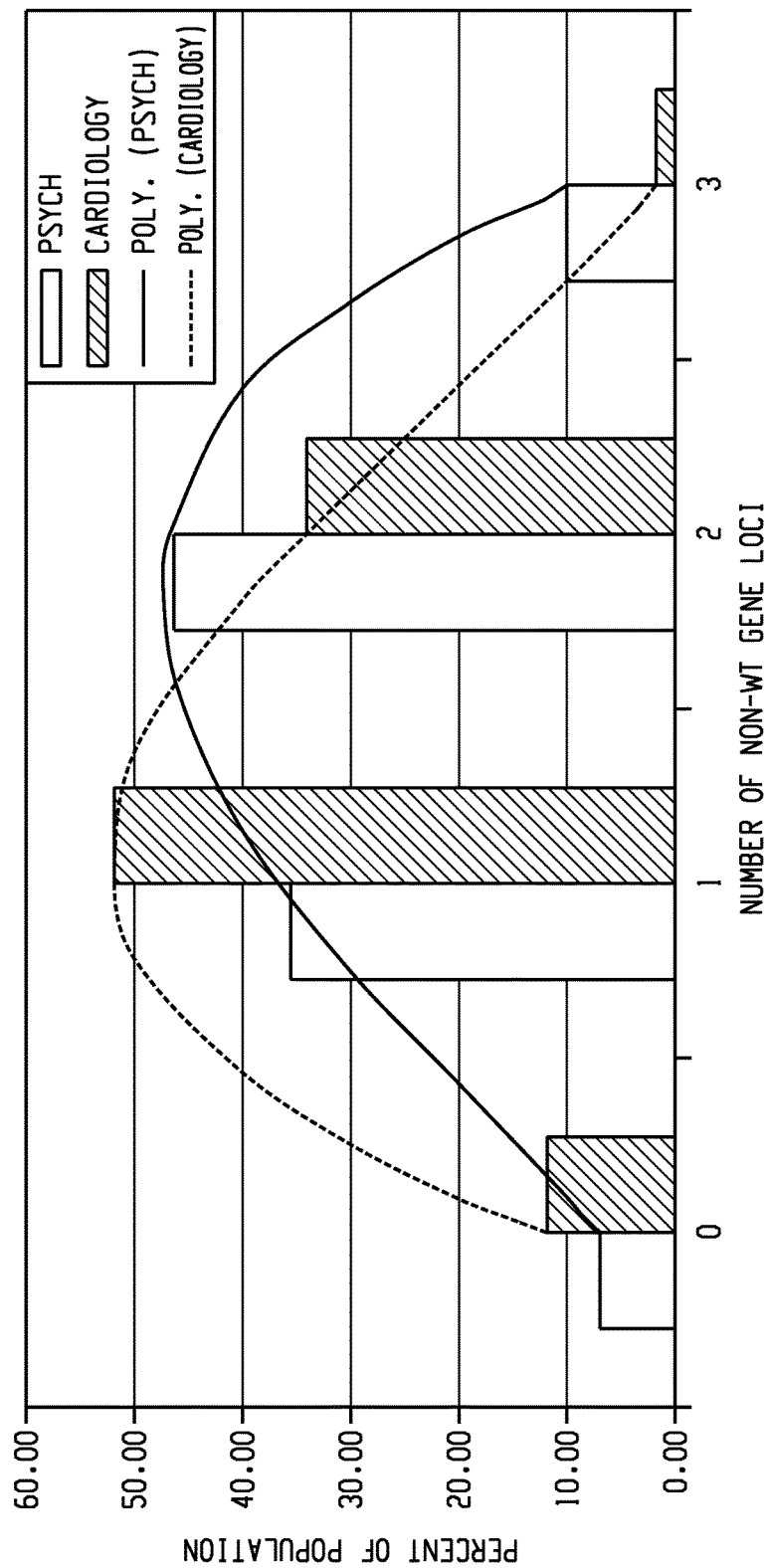
FIG. 14 shows the histogram by percentage for the Gene Alteration Index for 92 cardiovascular patients and 73 referred psychiatric outpatients.
Figure 15A:
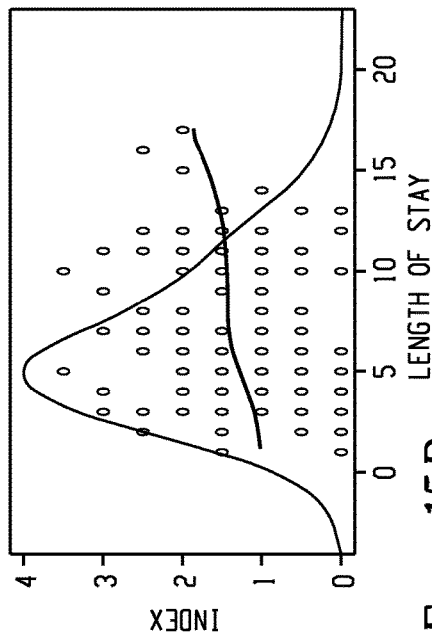
FIG. 15 depicts four physiogenomic plots that correlate length of stay with the four Drug Metabolism Reserve Physiotype indices of 150 hospitalized psychiatric patients.
Figure 15B:
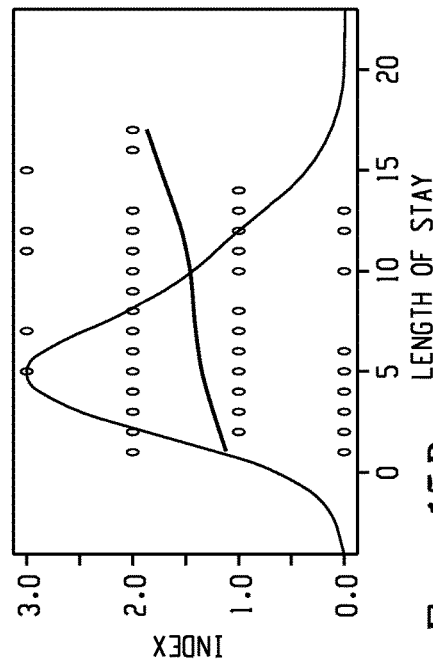
Figure 15C:
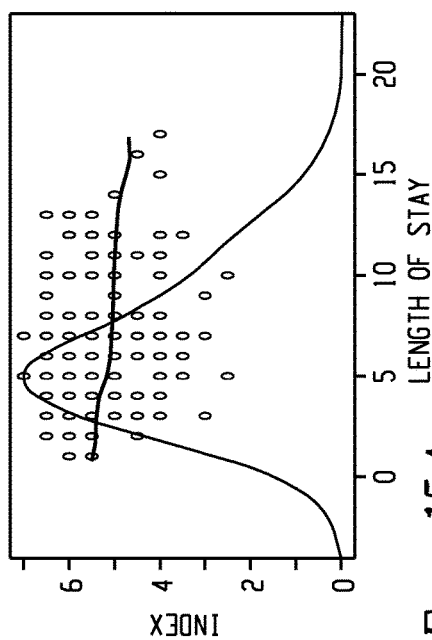
Figure 15D:
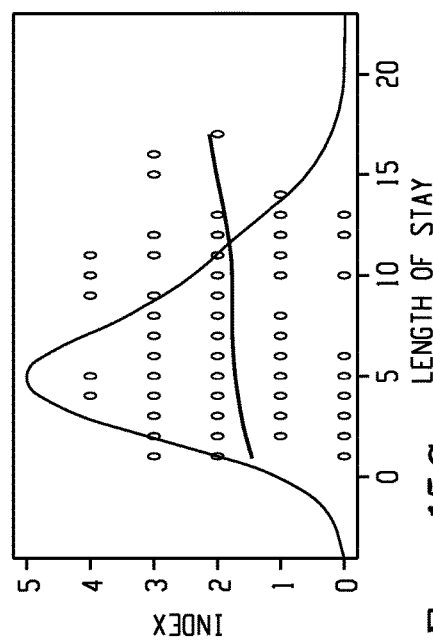

FIG. 14 compares the distributions of the Gene Alteration Index between the two cohorts ("Psych" refers to N=73 referred psychiatric outpatients, "Cardiology" refers to N=92 cardiology control patients). The increased departure from the control cohort demonstrated by the greater statistical significance when comparing the mean Drug Metabolism Reserve Physiotype index values suggests that this subset of individuals evidencing severe problems with psychotropic drug therapy have greater innate drug metabolism deficiencies. This highlights an even greater need for Drug Metabolism Reserve Physiotype analysis and guidance for patients referred to tertiary psychiatric hospitals.

Example 4

Clinical Correlations of Psychiatric Cohort

The cohort consists of 150 consecutive, consenting admissions ages 20-81 (median 43) 45% male, 55% female with a diagnosis of MDD and treated with psychotropic medications through the outpatient psychiatric services at the Institute of Living at Hartford Hospital (CT, USA), admitted January-March, 2007. They were referred to the Laboratory of Personalized Health at Genomas, Inc (CT, USA) for diagnostic genotyping as part of their clinical care because of efficacy or safety problems related to their medications. Self-reported ethnicities were 65% Caucasian, 28% Hispanic and 7% African-American. Data obtained included demographic, clinical and treatment information. Clinical data was acquired through a questionnaire given to patients at the time of enrollment. Treatment data was retrieved from paper and electronic medical records as well as questionnaire responses. CYP450 genotyping data were obtained for all 150 psychiatric patients on the CYP2C9, CYP2C19 and CYP2D6 genes.

Length of Hospitalization:

In comparing length of patient hospitalization with Drug Metabolism Reserve Physiotype indices, important correlations and trends were found, shown in Table 5. Those patients with a lower metabolic reserve (reserve index of 4 or less) had longer hospitalizations (7.7 vs. 6.1 days, p=0.023). Furthermore, individuals with an metabolic alteration index of 1.5 or less had an average length of hospitalization of 6.1 days, compared to 7.0 days for patients with an index greater than 1.5 (p=0.14). No significant correlation was found between length of hospitalization and the allele alteration index. Finally, the patients that were carriers of 3 non-WT CYP450 genes had an average length of stay of 9.6 days while the remainder of the patients had an average hospitalization of 6.2 days (p=0.038). Covariance (correlation with p<0.15) was found with three variables; race, age and whether or not the patient was taking an anti-psychotic. All correlations to Drug Metabolism Reserve Physiotype indices were calculated after correcting for this covariance.

TABLE 5

Length of stay data represents values after correcting for covariance.

| Index | Range | Count | Average Length of Hospitalization | Significance |
|---|---|---|---|---|
| Metabolic Reserve | ≤4 | 26 | 7.7 | p = 0.02 |
|  | >4 | 119 | 6.1 |  |
| Metabolic Alteration | ≤1.5 | 104 | 6.1 | p = 0.14 |
|  | >1.5 | 41 | 7.0 |  |
| Allele Alteration | ≤2 | 116 | 6.3 | p = 0.70 |
|  | >2 | 29 | 6.7 |  |
| Gene Alteration | ≤2 | 139 | 6.2 | p = 0.04 |
|  | >2 | 6 | 9.6 |  |

FIG. 15 depicts four physiogenomic plots that correlate length of stay with the four Drug Metabolism Reserve Physiotype indices. Plot 15a shows that length of stay increases as metabolic capacity as measure by the metabolic reserve decreases. Plots 15b-5d demonstrate that greater departure from wild-type alleles and genes leads to longer hospitalizations, however the relationship seen in 15c is not statistically significant.

Example 5

Drug Sensitivity Syndrome DSS

Based on the findings derived from comparisons to the control cohort and correlations with clinical variables, we have determined which individuals would qualify for categorization as harnessing a "Drug Sensitivity Syndrome" (DSS). Evidence from the studies described herein suggest that those individuals who carry altered alleles (rapid, deficient or null polymorphisms) on each of the three CYP450 genes in consideration represent the greatest departure from the control population and suffer the most severe clinical consequences.

Therefore we categorize the following: Drug Sensitivity Syndrome arises in individuals whose Gene Alteration Index is equal to 3. There are 36 individuals who carry polymorphisms in all three genes (6%). A detailed categorization of the polymorphisms per gene and carrier status for DSS patients is shown in Table 6.

Clinical symptoms associated with DSS as reported by physicians include "history of SSRI intolerance", "unusual response to several medications", and "multiple adverse drug reactions". Those individuals who fall into these categories will require additional care when being prescribed psychotropic medications due to their innate genetic drug metabolism alterations. Such an alert and appropriate guidance will be provided to the patient's physician and will include:

Patient's genotype for CYP2C9, CYP2C19 and CYP2D6
  Patient's metabolic profile based on Drug Metabolism Reserve Physiotype indices, including both written and graphical information to clarify the patient's absolute and relative drug metabolism capacities.
  List of psychotropic drugs that are substrates of these three genes with warnings associated with those drugs that are a substrate of a gene for which the patient has a deficiency.

TABLE 6

Detailed representation of Drug Sensitivity Syndrome population genotypes

| Number of polymorphisms | | |
|---|---|---|
| One each gene | Two each gene | N |
| 2C9, 2C19, 2D6 | — | 18 |
| 2C9, 2C19 | 2D6 | 16 |
| 2C9, 2D6 | 2C19 | 0 |
| 2C19, 2D6 | 2C9 | 1 |
| 2D6 | 2C9, 2C19 | 0 |
| 2C19 | 2C9, 2D6 | 0 |
| 2C9 | 2C19, 2D6 | 1 |
| — | 2C9, 2C19, 2D6 | 0 |
| TOTAL | | 36 |

A "phenotype" is a trait or collection of traits that is/are observable in an individual or population. The trait can be quantitative or qualitative.

A "polymorphism" is a locus that is variable; that is, within a population, the nucleotide sequence at a polymorphism has more than one version or allele. One example of a polymorphism is a "single nucleotide polymorphism" (SNP), which is a polymorphism at a single nucleotide position in a genome (the nucleotide at the specified position varies between individuals or populations).

A "locus" is a chromosomal position or region. For example, a polymorphic locus is a position or region where a polymorphic nucleic acid, trait determinant, gene or marker is located. A "gene locus" is a specific chromosome location in the genome of a species where a specific gene can be found.

A "marker" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, a cDNA, etc.), or from an encoded polypeptide. The term also refers to nucleic acid sequences complementary to or flanking the marker sequences, such as nucleic acids used as probes or primer pairs capable of amplifying the marker sequence.

A "gene" is one or more sequence(s) of nucleotides (that is a polynucleotide) in a genome that together encode one or more expressed molecule, e.g., an RNA, or polypeptide. The gene can include coding sequences that are transcribed into RNA, which may then be translated into a polypeptide sequence, and can include associated structural or regulatory sequences that aid in replication or expression of the gene.

A "set" of markers or probes refers to a collection or group of markers or probes, or the data derived therefrom, used for a common purpose, e.g., identifying an individual with a specified phenotype. Frequently, data corresponding to the markers or probes, or derived from their use, is stored in an electronic medium. While each of the members of a set possess utility with respect to the specified purpose, individual markers selected from the set as well as subsets including some, but not all of the markers, are also effective in achieving the specified purpose.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition consisting essentially of a plurality of primers that detect or amplify a plurality of polymorphisms in a gene CYP2C9 (SEQ ID NO:1) encoding the enzyme CYP2C9, a gene CYP2C19 (SEQ ID NO:2) encoding the enzyme CYP2C19 and a gene CYP2D6 encoding the enzyme CYP2D6 (SEQ ID NO:3) encoding the enzyme CYP2D6, the primers amplifying or detecting the following alleles:

| Gene | Allele | Nucleotide Change |
| --- | --- | --- |
| CYP2C9 | *1 | None |
|  | *2 | 430C > T |
|  | *3 | 1075A > C |
|  | *4 | 1076T > C |
|  | *5 | 1080C > G |
|  | *6 | 818delA |
| CYP2C19 | *1 | None |
|  | *2 | 681G > A |
|  | *3 | 636G > A |
|  | *4 | 1A > G |
|  | *5 | 1297C > T |
|  | *6 | 395G > A |
|  | *7 | IVS5 + 2T > A |
|  | *8 | 358T > C |
| CYP2D6 | *1 | None |
|  | *1XN | Gene copy number (N) |
|  | *2 | 1661G > C |
|  | *2a | −1584C > G |
|  | *2XN | Gene copy number (N) |
|  | *3 | 2549delA |
|  | *4 | 1846G > A |
|  | *4XN | Gene copy number (N) |
|  | *5 | Gene deletion |
|  | *6 | 1707delT |
|  | *7 | 2935A > C |
|  | *8 | 1758G > T |
|  | *9 | 2615_2617delAAG |
|  | *10 | 100C > T |
|  | *11 | 883G > C |
|  | *12 | 124G > A |
|  | *14 | 1758G > A |
|  | *15 | 137_138InsT |
|  | *17 | 1023C > T |
|  | *41 | 2988G > A | wherein the plurality of polymorphisms identify a combinatorial genotype for CYP2C9, CYP2C19 and CYP2D6, and wherein each primer comprises a detectable label, or wherein each primer is attached to a solid support.

\* \* \* \* \*

SEQUENCE LISTING

<160> NUMBER OF SEQ ID NOS: 3

<210> SEQ ID NO 1
<211> LENGTH: 1876
<212> TYPE: DNA
<213> ORGANISM: Homo sapiens

<400> SEQUENCE: 1

```
gtcttaacaa gaagagaagg cttcaatgga ttctcttgtg gtccttgtgc tctgtctctc      60
atgtttgctt ctcctttcac tctggagaca gagctctggg agaggaaaac tccctcctgg     120
ccccactcct ctcccagtga ttggaaatat cctacagata ggtattaagg acatcagcaa     180
atccttaacc aatctctcaa aggtctatgg ccctgtgttc actctgtatt ttggcctgaa     240
```

```
acccatagtg gtgctgcatg gatatgaagc agtgaaggaa gccctgattg atcttggaga    300
ggagttttct ggaagaggca ttttcccact ggctgaaaga gctaacagag gatttggaat    360
tgttttcagc aatggaaaga atggaaggat gatccggcgt ttctccctca tgacgctgcg    420
gaattttggg atggggaaga ggagcattga ggaccgtgtt caagaggaag cccgctgcct    480
tgtggaggag ttgagaaaaa ccaaggcctc accctgtgat cccactttca tcctgggctg    540
tgctccctgc aatgtgatct gctccattat tttccataaa cgttttgatt ataaagatca    600
gcaatttctt aacttaatgg aaaagttgaa tgaaaacatc aagatttttga gcagcccctg    660 gatccagatc tgcaataatt tttctcctat cattgattac ttcccgggaa ctcacaacaa    720
attacttaaa aacgttgctt ttatgaaaag ttatattttg gaaaagtaa aagaacacca    780 agaatcaatg acatgaaca accctcagga ctttattgat tgcttcctga tgaaaatgga    840
gaaggaaaag cacaaccaac catctgaatt tactattgaa agcttggaaa acactgcagt    900
tgacttgttt ggagctggga cagagacgac aagcacaacc ctgagatatg ctctccttct    960
cctgctgaag cacccagagg tcacagctaa agtccaggaa gagattgaac gtgtgattgg   1020
cagaaaccgg agccctgca tgcaagacag gagccacatg ccctacacag atgctgtggt   1080
gcacgaggtc cagagataca ttgaccttct ccccaccagc ctgccccatg cagtgacctg   1140
tgacattaaa tcagaaact atctcattcc caagggcaca accatattaa tttccctgac   1200
ttctgtgcta catgacaaca agaatttcc caacccagag atgtttgacc ctcatcactt   1260
tctggatgaa ggtggcaatt ttaagaaaag taaatacttc atgccttttct cagcaggaaa   1320 acggatttgt gtgggagaag ccctggccgg catggagctg ttttattcc tgacctccat   1380 tttacagaac tttaacctga aatctctggt tgacccaaag aaccttgaca ccactccagt   1440
tgtcaatgga tttgcctctg tgccgccctt ctaccagctg tgcttcattc ctgtctgaag   1500
aagagcagat ggcctggctg ctgctgtgca gtccctgcag ctctctttcc tctggggcat   1560
tatccatctt tcactatctg taatgccttt tctcacctgt catctcacat tttcccttcc   1620
ctgaagatct agtgaacatt cgacctccat tacggagagt ttcctatgtt tcactgtgca   1680
aatatatctg ctattctcca tactctgtaa cagttgcatt gactgtcaca taatgctcat   1740
acttatctaa tgttgagtta ttaatatgtt attattaaat agagaaatat gatttgtgta   1800
ttataattca aaggcatttc ttttctgcat gttctaaata aaaagcatta ttatttgctg   1860
aaaaaaaaaa aaaaaa                                                   1876
```

<210> SEQ ID NO 2
<211> LENGTH: 1473
<212> TYPE: DNA
<213> ORGANISM: Homo sapiens

<400> SEQUENCE: 2

```
atggatcctt ttgtggtcct tgtgctctgt ctctcatgtt tgcttctcct ttcaatctgg     60
agacagagct ctgggagagg aaaactccct cctggcccca ctcctctccc agtgattgga   120
aatatcctac agatagatat taaggatgtc agcaaatcct taaccaatct ctcaaaaatc   180
tatgcccctg tgttcactct gtatttggc ctggaacgca tggtggtgct gcatggatat   240
gaagtggtga ggaagcccct gattgatctt ggagaggagt tttctggaag aggccatttc   300
ccactggctg aaagagctaa cagaggattt ggaatcgttt tcagcaatgg aaagagatgg   360
aaggagatcc ggcgtttctc cctcatgacg ctgcggaatt ttgggatggg gaagaggagc   420
```

```
attgaggacc gtgttcaaga ggaagcccgc tgccttgtgg aggagttgag aaaaaccaag    480
gcttcaccct gtgatcccac tttcatcctg ggctgtgctc cctgcaatgt gatctgctcc    540
attattttcc agaaacgttt cgattataaa gatcagcaat ttcttaactt gatggaaaaa    600
ttgaatgaaa acatcaggat tgtaagcacc ccctggatcc agatatgcaa taattttccc    660
actatcattg attatttccc gggaacccat aacaaattac ttaaaaacct tgcttttatg    720
gaaagtgata ttttggagaa agtaaaagaa caccaagaat cgatggacat caacaaccct    780
cgggacttta ttgattgctt cctgatcaaa atggagaagg aaaagcaaaa ccaacagtct    840
gaattcacta ttgaaaactt ggtaatcact gcagctgact tacttggagc tgggacagag    900
acaacaagca caaccctgag atatgctctc cttctcctgc tgaagcaccc agaggtcaca    960
gctaaagtcc aggaagagat tgaacgtgtc attggcagaa accggagccc ctgcatgcag   1020
gacaggggcc acatgcccta cacagatgct gtggtgcacg aggtccagag atacatcgac   1080
ctcatcccca ccagcctgcc ccatgcagtg acctgtgacg ttaaattcag aaactacctc   1140
attcccaagg gcacaaccat attaacttcc ctcacttctg tgctacatga caacaaagaa   1200
tttcccaacc cagagatgtt tgaccctcgt cactttctgg atgaaggtgg aaattttaag   1260
aaaagtaact acttcatgcc tttctcagca ggaaaacgga tttgtgtggg agagggcctg   1320
gcccgcatgg agctgttttt attcctgacc ttcattttac agaactttaa cctgaaatct   1380
ctgattgacc aaaggaccct tgacacaact cctgttgtca atggatttgc ttctgtcccg   1440
cccttctatc agctgtgctt cattcctgtc tga                                1473

<210> SEQ ID NO 3
<211> LENGTH: 1673
<212> TYPE: DNA
<213> ORGANISM: Homo sapiens

<400> SEQUENCE: 3
gtgctgagag tgtcctgcct ggtcctctgt gcctggtggg gtggggtgc caggtgtgtc      60
cagaggagcc catttggtag tgaggcaggt atggggctag aagcactggt gcccctggcc    120
gtgatagtgg ccatcttcct gctcctggtg gacctgatgc accggcgcca acgctgggct    180
gcacgctacc caccaggccc cctgccactg cccgggctgg gcaacctgct gcatgtggac    240
ttccagaaca caccatactg cttcgaccag ttgcggcgcc gcttcgggga cgtgttcagc    300
ctgcagctgg cctggacgcc ggtggtcgtg ctcaatgggc tggcggccgt gcgcgaggcg    360
ctggtgaccc acggcgagga caccgccgac cgccccgcct gcccatcac ccagatcctg    420
ggtttcgggc gcgttccca aggggtgttc ctggcgcgct atgggcccgc gtggcgcgag    480
cagaggcgct tctccgtctc caccttgcgc aacttgggcc tgggcaagaa gtcgctggag    540
cagtgggtga ccgaggaggc cgcctgcctt tgtgccgcct tcgccaacca ctccggacgc    600
cccttttcgcc ccaacggtct cttggacaaa gccgtgagca acgtgatcgc ctccctcacc    660
tgcgggcgcc gcttcgagta cgacgaccct cgcttcctca ggctgctgga cctagctcag    720
gagggactga aggaggagtc gggctttctg cgcgaggtgc tgaatgctgt cccgtcctc     780
ctgcatatcc cagcgctggc tggcaaggtc ctacgcttcc aaaaggcttt cctgacccag    840
ctggatgagc tgctaactga gcacaggatg acctgggacc cagcccagcc ccccgagac     900
ctgactgagg ccttcctggc agagatggag aaggccaagg ggaaccctga gagcagcttc    960
aatgatgaga acctgtgcat agtggtggct gacctgttct ctgccgggat ggtgaccacc   1020
tcgaccacgc tggcctgggg cctcctgctc atgatcctac atccggatgt gcagcgccgt   1080
```

```
gtccaacagg agatcgacga cgtgataggg caggtgcggc gaccagagat gggtgaccag    1140
gctcacatgc cctacaccac tgccgtgatt catgaggtgc agcgctttgg ggacatcgtc    1200
cccctgggtg tgacccatat gacatcccgt gacatcgaag tacagggctt ccgcatccct    1260
aagggaacga cactcatcac caacctgtca tcggtgctga aggatgaggc cgtctgggag    1320
aagcccttcc gcttccaccc cgaacacttc ctggatgccc agggccactt tgtgaagccg    1380
gaggccttcc tgcctttctc agcaggccgc cgtgcatgcc tcggggagcc cctggccgc     1440 atggagctct tcctcttctt cacctccctg ctgcagcact tcagcttctc ggtgcccact    1500
ggacagcccc ggcccagcca ccatggtgtc tttgctttcc tggtgacccc atcccctat     1560 gagctttgtg ctgtgccccg ctagaatggg gtacctagtc cccagcctgc tccctagcca    1620
gaggctctaa tgtacaataa agcaatgtgg tagttccaaa aaaaaaaaaa aaa           1673
```